(12) United States Patent
Stöckemann et al.

(10) Patent No.: US 7,309,691 B2
(45) Date of Patent: Dec. 18, 2007

(54) COMBINED PHARMACEUTICAL PREPARATION CONTAINING LHRH-ANALOGOUS SUBSTANCES AND ANTI ESTROGENS FOR TREATING GYNAECOLOGICAL DISORDERS

(75) Inventors: Klaus Stöckemann, Berlin (DE); Peter Muhn, Berlin (DE)

(73) Assignee: Achering Aktiengesellschaft, Berlin (DE)

( * ) Notice: Subject to any disclaimer, the term of this patent is extended or adjusted under 35 U.S.C. 154(b) by 1101 days.

(21) Appl. No.: 09/117,357

(22) PCT Filed: Jan. 29, 1997

(86) PCT No.: PCT/EP97/00395

§ 371 (c)(1),
(2), (4) Date: Sep. 22, 1998

(87) PCT Pub. No.: WO97/27863

PCT Pub. Date: Aug. 7, 1997

(65) Prior Publication Data

US 2001/0041672 A1    Nov. 15, 2001

(30) Foreign Application Priority Data

Jan. 29, 1996   (DE) .................. 196 04 231

(51) Int. Cl.
*A61K 38/00* (2006.01)
*A61K 31/445* (2006.01)

(52) U.S. Cl. ............................. 514/16; 514/2; 514/324

(58) Field of Classification Search ............. 514/2, 514/15, 800, 874, 313, 324; 530/313
See application file for complete search history.

(56) References Cited

U.S. PATENT DOCUMENTS

| | | | | |
|---|---|---|---|---|
| 5,395,842 A | * | 3/1995 | Labrie et al. | 514/320 |
| 5,451,590 A | * | 9/1995 | Dodge | 514/324 |
| 5,457,116 A | * | 10/1995 | Black et al. | 514/324 |
| 5,552,417 A | * | 9/1996 | Dodge | 514/324 |
| 5,593,987 A | * | 1/1997 | Cullinan et al. | 514/217.03 |
| 5,843,962 A | * | 12/1998 | Dodge | 514/324 |
| 6,096,764 A | * | 8/2000 | Bryant et al. | 514/324 |

FOREIGN PATENT DOCUMENTS

EP    0 897 721 A2    2/1999

OTHER PUBLICATIONS

Robertson et al., Horm. Res. 1989: 32 (suppl 1):206-208.*
Walker et al., Eur. J. Cancer Clin. Oncol., vol. 25, No. 4, 651-654, 1989.*
Monsonego et al., Am. J. Obstet Gynecol., 1991: 164: 1181-9.*
Goulding et al., Bone and Mineral, 18(2), 143-152 (1992).*
Devogelaer JP et al., "LHRH analogues and bone loss", Lancet, Jun. 27, 1987; 1(8548): 1498.*

* cited by examiner

*Primary Examiner*—Raymond J. Henley, III
(74) *Attorney, Agent, or Firm*—Millen, White, Zelano. Branigan, P.C.

(57) ABSTRACT

The invention relates to a pharmaceutical combined preparation of LHRH analogues and anti-oestrogens having tissue-selective oestrogen activity and also to its use for the treatment of gynaecological disorders, especially for the treatment of endometrioses and myomas.

21 Claims, No Drawings

COMBINED PHARMACEUTICAL PREPARATION CONTAINING LHRH-ANALOGOUS SUBSTANCES AND ANTI ESTROGENS FOR TREATING GYNAECOLOGICAL DISORDERS

The invention relates to a pharmaceutical combined preparation of LHRH analogues and anti-oestrogens having a tissue-selective oestrogenic activity, and also to its use for the treatment of gynaecological disorders, especially for the treatment of endometrioses and myomas.

BACKGROUND OF THE INVENTION

Gynaecological disorders and diseases considerably reduce the quality of life of women and frequently result, in some cases in addition to unbearable pain, in infertility. One of the most common diseases in women of child-bearing age (5% to 10%) is endometriosis. Associated with it are severe pain during menstruation and a limited fertility rate to sterility. In the case of the myoma, a benign tumour in the muscle tissue of the uterus, the incidence is high too (in 10 to 25% of women in their 30s). Myomas may cause heavy abnormal menstrual bleeding (hypermenorrhoea), painful menstruation (dysmenorrhoea) and/or intermenstrual bleeding (metrorrhagia, menorrhagia) and each, depending on the condition, may also result in limited fertility. In addition to dysmenorrhoea caused by endometriosis and by myomas, dysmenorrhoea that is caused by functional disorders (by hormonal and vegetative disorders) also occurs.

The gonal steroids (oestrogens, gestagens), which are under the control of the hypothalamic-pituitary system, and growth factors (including also cytokines) play a decisive role in the clinical syndromes described. Treatment of such diseases and disorders is usually effected with hormones, such as LHRH analogues (Lemay, A. et al., Fertil. Steril., 41, 863-871 (1984)). In some women, however, these are not tolerated without side effects. For example, it is known that treatment with LHRH agonists may result in side effects such as, for example, hypo-oestrogenaemia (risk of osteoporosis) (Dawood, M. Y. et al., Fertil. Steril. 52, 21-25, (1989)) and treatment with danazol may result in androgenisation phenomena (Dmowski, W. P. et al., Am. J. Obstet. Gynecol., 130, 41-48 (1978)).

No established and proven long-term medicament treatment has existed hitherto for myomas. The medicament treatment currently used is associated with distinct side effects. For example, the use of LHRH agonists for more than six months results in a hypo-oestrogenic state in women (Matta, W. H. et al., Br. Med. J., 294, 1523-1525, (1987)) and, associated with that, a reduction in bone density, which increases the risk of osteoporosis (Dawood, M. Y. Int. J. Gynecol. Obstet., 40, 29-42 (1993)). Other side effects associated with oestrogen withdrawal (hot flashes) are also described by Dawood.

Studies for the treatment of gynaecological disorders with LHRH analogues and oestrogens—so-called Add-Back or HRT treatment regimes—are known for the purpose of avoiding those side effects. The discovery of an oestrogen dose that completely prevents a reduction in bone density using LHRH agonist therapy (Howell, R. et al., Fertil, Steril. 64, 474-481, (1995)) without at the same time stimulating endometriosis or stimulating the endometrium, which may result in endometrium hyperplasia and, associated with that, endometrium carcinomas, has hitherto been unsuccessful, however.

SUMMARY OF THE INVENTION

The problem underlying the invention is therefore to prepare a pharmaceutical combined preparation for the treatment of gynaecological disorders, especially for the treatment of endometrioses and myomas, with which a reduction in bone density is prevented and the disadvantages of previous hormone treatments are avoided.

DETAILED DESCRIPTION OF THE INVENTION

The problem is solved in accordance with the invention by a pharmaceutical combined preparation that comprises two active ingredients, the first of which is an LHRH analogue or a combination of LHRH analogues and the second of which is an anti-oestrogen having tissue-selective oestrogenic activity.

The LHRH analogue is an LHRH agonist or antagonist. Any LHRH antagonist or LHRH agonist may be used within the scope of the invention. Preferred LHRH analogues are selected from the group of compounds Leuprorelin, Cetrorelix, Antide, Buserelin, Ramorelix, Zoladex, 2-(4-acetylaminophenyl)-4,7-dihydro-7-(2-methoxybenzyl)-3-(N-methyl-N-benzylaminomethyl)-4-oxothieno[2,3-b]pyridine-5-carboxylic acid ethyl ester and 5-benzoyl-7-(2,6-difluorobenzyl)-4,7-dihydro-3-(N-methyl-N-benzylaminomethyl)-2-(4-propionylamidophenyl)-4-oxothieno[2,3-b]pyridine.

The active ingredients are generally in separate forms of administration or, in the case of orally bioavailable LHRH antagonists, also in a joint form of administration.

The LHRH analogues preferably used are known and are described in the patent specifications U.S. Pat. No. 4,005,063 (Leuprorelin), EP-B1 0 299 402 (Cetrorelix), GB 1 523 623 (Buserelin), EP-A 0 451 791 (Ramorelix), WO-A 89/01944 (Antide), WO-A 92/20711 (Ac-D-Nal-D-Cpa-D-Pal-Ser-Tyr-D-Cit-Leu-Lys(Mor)-Pro-D-Ala-NH$_2$), U.S. Pat. No. 4,100,274 (Zoladex) and WO-A 95/28405 (2-(4-acetylaminophenyl)-4,7-dihydro-7-(2-methoxybenzyl)-3-(N-methyl-N-benzylaminomethyl)-4-oxothieno[2,3-b]pyridine-5-carboxylic acid ethyl ester).

They are prepared and packaged according to processes known per se and, depending on the desired use, are available in oral or nasal form, in the form of an injection, or in the form of a long-term preparation to be administered topically or intravaginally. According to the invention, the LHRH analogues may be administered as individual doses or as depot forms.

A unit dose contains different amounts of active ingredient depending in each case on the form of administration. For example, in the case of oral administration usually from 2 μg to 20 mg of LHRH analogue is administered per kg of body weight. The administration may be in solid or liquid form. For intravenous, subcutaneous, intramuscular, intranasal or intravaginal administration, the amounts of LHRH analogues are from 0.02 μg to 2.5 mg per kg of body weight. For parenteral administration there is preferably used an isotonic sodium chloride or dextrose solution that optionally is adjusted with a buffer to a pH value of from 5 to 9, preferably to the pH value of the blood.

Leuprorelin is preferably used orally at a dose of from 2 to 100 μg/kg of body weight (daily dose); one tablet contains preferably from 0.1 to 5.0 mg of Leuprorelin. The dose for parenteral administration is preferably from 0.02 to 1.0 μg/kg of body weight.

Cetrorelix is used preferably in the form of a physiological saline with an amount of active ingredient of from 0.1 to 2.5 mg/kg of body weight. In DE 43 42 092, also slow-release formulations of Cetrorelix are described.

Buserelin is administered preferably in the following doses:
from 0.02 to 1 µg/kg of body weight (intravenous),
from 0.02 to 2 µg/kg of body weight (subcutaneous),
from 0.02 to 10 µg/kg of body weight (intramuscular),
from 0.1 to 50 µg/kg of body weight (intranasal) and
from 10 to 200 µg/kg of body weight (oral).

As in the case of Cetrorelix, slow-release formulations are also possible. In the case of an implant, the implant contains from 1 to 6 mg of Cetrorelix.

Zoladex is preferably administered orally with a content of from 50 µg to 20 mg/kg of body weight and parenterally with a content of from 0.02 µg to 100 µg/kg of body weight or using a slow-release system (WO-A 93/24150).

Antide is, like Cetrorelix, administered in an amount of from 0.1 to 2.5 mg/kg of body weight.

The administration of Ramorelix is carried out preferably in liposomal form.

Depot formulations for peptides (microparticles, implants) are described inter alia in EP 0 505 966 and EP 0 315 875.

According to the invention, the second active ingredient component of the combined preparation is an anti-oestrogen having tissue-selective oestrogenic activity.

Anti-oestrogenic substances are used inter alia in tumour therapy.

Within the scope of the invention there are to be understood by anti-oestrogens having tissue-selective oestrogenic activity so-called SERMs (selective oestrogen-receptor modulators) which exert their partial agonistic oestrogenic activity tissue- and organ-selectively.

Any antioestrogen having tissue-selective oestrogenic activity may be used in accordance with the invention. Preferably used are those selected from the group Raloxifen, Droloxifen, Centchroman and derivatives thereof. Anti-oestrogens of the Raloxifen type are especially preferred.

The anti-oestrogens mentioned are known. For example Raloxifen is 6-hydroxy-2-(4-hydroxyphenyl)-3-[4-(2-piperidinoethoxy)benzoyl]benzo[b]thiophene. In combination with parathyroid hormone, Raloxifen and its derivatives are used to increase bone mass. EP 0635 270 discloses that raloxifene is described in U.S. Pat. No. 4,418,068 and that EP-A-584952 discloses that raloxifene is useful in the inhibition or preventing of bone loss.

The active ingredient content of the anti-oestrogen used in accordance with the invention is in the case of daily administration from 0.1 µg to 10 mg of antioestrogen per kg of body weight, depending on the form of administration. The anti-oestrogens may be administered intravenously, subcutaneously, intramuscularly, orally, intranasally or intravaginally. Slow-release formulations are also possible, in which case the amount released daily lies also within the above-mentioned range.

The administration of the LHRH analogue and of the anti-oestrogen to the patient may be simultaneous and/or chronologically sequential. Various treatment regimes are possible:

1. The LHRH analogue is administered simultaneously with the tissue-selective anti-oestrogen over the same period of time. Administration is possible daily, every three days, weekly or once monthly over a period of from 1 to 6 months. Longer administration is also readily possible. In the case of monthly administration a depot formulation is preferred.

2. The LHRH analogue is first of all administered simultaneously with the tissue-selective anti-oestrogen over a particular period of time. The information given in 1 applies in respect of period and frequency of administration (daily or at greater intervals). Treatment is then continued with the anti-oestrogen only. Here, too, the information given in 1 applies in respect of period and frequency of administration.

3. The treatment with the LHRH analogue is conducted over a particular period of time and terminated. Following this the tissue-selective anti-oestrogen is then administered. For each component, the period and frequency of administration may be selected as indicated in 1.

It was established that the treatment with the combined preparation according to the invention surprisingly prevents the hitherto observed LHRH analogue-induced reduction in bone density, and the endometriosis, inhibited in its growth, is not stimulated again, and the growth of the normal endometrium in the uterus also is not stimulated.

The pharmaceutical combined preparation according to the invention is suitable especially for long-term treatment of endometrioses and myomas and other steroid(sex)-hormone-dependent disorders, since on the one hand the side effects that normally occur with an LHRH analogue (agonist or antagonist) treatment are avoided and on the other hand lost bone mass is rebuilt (for example in the case of administration of the tissue-selective anti-oestrogen after completion of an LHRH analogue treatment). At the same time the growth inhibition of the endometriosis is maintained without the endometrium in the uterus being stimulated.

Variant 1 has proved especially preferred for long-term therapy.

The pharmaceutical combined preparation according to the invention is prepared, for example, by formulating the LHRH analogues and the anti-oestrogens having tissue-selective oestrogenic activity separately from one another with the customary pharmaceutical carriers, excipients and/or additives; the forms of administration of the individual active ingredients do not have to be identical. It is wholly possible, for example, for one active ingredient of the combined preparation to be administered orally while the other active ingredient is administered subcutaneously or nasally.

In the case of orally bioavailable LHRH analogues, it is also possible for the two active ingredients (LHRH analogues plus anti-oestrogen) to be formulated together for oral administration. Separate oral forms of administration are also possible.

The invention relates also to a packaging unit which, in the case of peptidergic LHRH analogues, comprises at least three components. The unit contains two spatially separately packaged active ingredients, one of which is an LHRH analogue or a combination of LHRH analogues, and the other of which is an anti-oestrogen having tissue-selective oestrogenic activity. The third component is an information leaflet for the simultaneous and/or chronologically sequential administration of the forms of administration.

The invention relates also to the use of an LHRH analogue or a combination of LHRH analogues and an anti-oestrogen having tissue-selective oestrogenic activity for the treatment of gynaecological disorders, especially for the treatment of endometrioses and myomas.

The invention is illustrated further in the following by Examples without, however, being limited to those Examples.

EMBODIMENT EXAMPLES

Example 1

Effect of LHRH Administration and Raloxifen Administration on Experimentally Produced Endometriosis in the Rat 1.1 Comparison of the administration of each of the active ingredient components alone with the simultaneous administration of the active ingredients (combined preparation)

Method:

Fragments of endometrium were transplanted into different regions of the abdominal cavity of 60 animals.

Four weeks later the development of the endometriosis (cystic endometriosis foci) was examined.

The animals were then treated for 4 weeks with the LHRH antagonists Antide (0.5 mg/animal every 3 days s.c.) and Raloxifen (3 mg/animal per day p.o.) in each case alone, or in a combination of the two compounds. At the end the size of the endometriosis foci before the beginning of the treatment was compared with the values after 4 weeks' treatment.

The combination of LHRH antagonist plus Raloxifen resulted in a complete regression of the endometriosis without there being a significant reduction in bone mass. At the same time no oestrogenic effects on the uterus (no stimulation of the endometrium) were observed.

By comparison, although treatment with the LHRH antagonists alone resulted in a complete regression of the endometriosis foci, at the same time it caused a reduction in endogenous oestrogen levels corresponding to an ovariectomy. The result was a distinct reduction in bone density and an increase in osteoclast activity.

Administration of Raloxifen alone resulted in a partial regression of the endometriosis.

1.2. LHRH antagonist Antide and Raloxifen for simultaneous and chronologically sequential administration 60 animals received the LHRH antagonist Antide and Raloxifen in parallel for the first 2 weeks and Raloxifen alone for the following 2 weeks. The doses were selected as in 1.1.

As with the simultaneous administration of the active ingredients, the result to be recorded was a complete regression of the endometriosis without a significant reduction in bone mass. At the same time there were no oestrogenic effects on the uterus.

1.3. Chronologically sequential administration of the combined preparation 60 animals received the LHRH antagonist Antide for 2 weeks. On completion of the LHRH administration Raloxifen was then administered for 2 weeks.

This sequential treatment also resulted in 100% regression of the endometriosis without a reduction in bone density.

Example 2

Analogously to Example 1, treatment with LHRH antagonists Ac-D-Nal-D-Cpa-D-Pal-Ser-Tyr-D-Cit-Leu-Lys(Mor)-D-Ala-$NH_2$ and Droloxifen was carried out on 40 animals. The same results could be achieved as in Example 1.

The invention claimed is:

1. A method for ameliorating LHRH analogue-induced reduction in bone density in a patient comprising administering to said patient one or more LHRH analogues and Raloxifen wherein said one or more LHRH analogues and Raloxifen are administered sequentially or simultaneously.

2. A method according to claim 1, wherein said LHRH analogue is an LHRH agonist.

3. A method according to claim 1, wherein said LHRH analogue is Leuprorelin, Cetrorelix, Buserelin, Antide, Ac-D-Nal-D-Cpa-D-Pal-Ser-Tyr-D-Cit-Leu-Lys(Mor)-Pro-D-Ala-$NH_2$, Ramorelix, or Zoladex.

4. A method according to claim 1, wherein said one or more LHRH analogues is orally bioavailable.

5. A method according to claim 1, wherein said one or more LHRH analogues is a non-peptidergic LHRH agonist or non-peptidergic LHRH antagonist.

6. A method according to claim 1, wherein said LHRH analogue is an LHRH antagonist.

7. A method according to claim 1, wherein said LHRH analogue is administered in the amount of 2 μg-20 mg per kilogram of body weight and Raloxifen is administered in an amount of 0.1 μg-10 mg per kilogram of body weight.

8. A method according to claim 1, wherein said LHRH analogue is peptidergic.

9. A method according to claim 1, wherein said LHRH analogue is Leuprorelin, Cetrorelix, Buserelin, Antide, Ac-D-Nal-D-Cpa-D-Pal-Ser-Tyr-D-Cit-Leu-Lys(Mor)-Pro-D-Ala-$NH_2$, Ramorelix, Zoladex or combinations thereof.

10. A method according to claim 1, wherein Raloxifen is administered after administration of said LHRH analogue.

11. A method according to claim 1, wherein said LHRH analogue is Leuprorelin, Cetrorelix, Antide, Ac-D-Nal-D-Cpa-D-Pal-Ser-Tyr-D-Cit-Leu-Lys(Mor)-Pro-D-Ala-$NH_2$, Ramorelix, or Zoladex.

12. A method according to claim 11, wherein said LHRH analogue is Antide.

13. A method according to claim 11, wherein said LHRH analogue is Ac-D-Nal-D-Cpa-D-Pal-Ser-Tyr-D-Cit-Leu-Lys(Mor)-Pro-D-Ala-$NH_2$.

14. A method of inhibiting LHRH analog-induced detrimental side effects due to the administration of an LHRH analog to a patient, wherein said detrimental side effect is reduction in bone density, comprising administering to a patient in need thereof an effective amount of Raloxifen.

15. A method according to claim 14, wherein said patient is a woman.

16. A method according to claim 15, wherein Raloxifen is administered orally.

17. A method according to claim 14, wherein said LHRH analog is Leuprorelin, Buserelin or Zoladex.

18. A method for ameliorating LHRH analogue-induced reduction in bone density in a patient comprising administering to said patient one or more LHRH analogues and Raloxifen or the hydrochloride salt thereof wherein said one or more LHRH analogues and Raloxifen, or the hydrochloride salt, are administered sequentially or simultaneously.

19. A method of inhibiting LHRH analog-induced detrimental side effects due to the administration of an LHRH analog to a patient, wherein said detrimental side effect is reduction in bone density, comprising administering to a patient in need thereof an effective amount of Raloxifen or the hydrochloride salt thereof.

20. A method for ameliorating LHRH analogue-induced reduction in bone density in a patient comprising administering to said patient one or more LHRH analogues and 6-hydroxy-2-(4-hydroxyphenyl)-3-[4-(2-piperidinoethoxy)-benzoyl]benzo[b]thiophene, or the hydrochloride salt thereof, wherein said one or more LHRH analogues and 6-hydroxy-2-(4-hydroxyphenyl)-3-[4-(2-piperidinoethoxy)- benzoyl]benzo[b]thiophene, or the hydrochloride salt thereof, are administered sequentially or simultaneously.

21. A method of inhibiting LHRH analog-induced detrimental side effects due to the administration of an LHRH analog to a patient, wherein said detrimental side effect is reduction in bone density, comprising administering to a patient in need thereof an effective amount of 6-hydroxy-2-(4-hydroxyphenyl)-3-[4-(2-piperidinoethoxy)benzoyl]benzo [b]-thiophene.

* * * * *

UNITED STATES PATENT AND TRADEMARK OFFICE
CERTIFICATE OF CORRECTION

PATENT NO.         : 7,309,691 B2
APPLICATION NO. : 09/117357
DATED              : December 18, 2007
INVENTOR(S)        : Klaus Stöckemann et al.

It is certified that error appears in the above-identified patent and that said Letters Patent is hereby corrected as shown below:

On the title page item (73), "Achering" should read -- Schering --
Column 6, line 66, reads "LHRH analogues and" should read -- LHRH analogues and said --

Signed and Sealed this

Nineteenth Day of August, 2008

JON W. DUDAS
*Director of the United States Patent and Trademark Office*